United States Patent [19]
Dillow

[11] Patent Number: 5,916,198
[45] Date of Patent: Jun. 29, 1999

[54] NON-BINDING SURGICAL VALVE

[75] Inventor: David Curtis Dillow, Cupertino, Calif.

[73] Assignee: FemRx, Inc., Sunnyvale, Calif.

[21] Appl. No.: 08/906,308

[22] Filed: Aug. 5, 1997

[51] Int. Cl.[6] .............................................. A61M 5/178
[52] U.S. Cl. .......................... 604/167; 604/171; 606/185
[58] Field of Search .................................. 604/167, 171, 604/236, 237, 243; 606/185

[56]  References Cited

U.S. PATENT DOCUMENTS

| | | | |
|---|---|---|---|
| 4,909,798 | 3/1990 | Fleischhacker et al. | 604/256 |
| 5,141,498 | 8/1992 | Christian | 604/167 |
| 5,180,373 | 1/1993 | Green et al. | 604/167 |
| 5,263,944 | 11/1993 | Vidal et al. | 604/256 |
| 5,269,764 | 12/1993 | Vetter et al. | 604/167 |
| 5,300,033 | 4/1994 | Miller | 604/167 |
| 5,312,362 | 5/1994 | Pfolsgraf et al. | 604/167 |
| 5,330,437 | 7/1994 | Durman | 604/167 |
| 5,350,364 | 9/1994 | Stephens et al. | 604/167 |
| 5,354,280 | 10/1994 | Haber et al. | 604/167 |
| 5,356,394 | 10/1994 | Farley et al. | 604/254 |
| 5,380,288 | 1/1995 | Hart et al. | 604/167 |
| 5,385,552 | 1/1995 | Haber et al. | 604/167 |
| 5,389,080 | 2/1995 | Yoon | 604/167 |
| 5,391,153 | 2/1995 | Haber et al. | 604/167 |
| 5,397,314 | 3/1995 | Farley et al. | 604/256 |
| 5,401,248 | 3/1995 | Bencini | 604/167 |
| 5,429,609 | 7/1995 | Yoon | 604/167 |
| 5,441,486 | 8/1995 | Yoon | 604/167 |
| 5,496,280 | 3/1996 | Vandenbroek et al. | 604/167 |
| 5,514,098 | 5/1996 | Pfoslgraf et al. | 604/167 |
| 5,603,702 | 2/1997 | Smith et al. | 604/256 |
| 5,662,615 | 9/1997 | Blake, III | 604/167 |

*Primary Examiner*—Michael Buiz
*Assistant Examiner*—Lien Ngo

[57]  ABSTRACT

A surgical valve prevents loss of insufflation gas (or the like) when no instrument traverses the valve lumen. The valve is suitable for passing surgical implements distally, and for passing enlarged bodies (such as large morcels of severed tissue) proximally. A first set of valve segments angle together along a slit, similar to a duck-bill valve. A second set of valve segments angle outwardly distally, the second segments often having a passage so that distal pressure pushes the first segments together along the slit.

7 Claims, 7 Drawing Sheets

NON-BINDING SURGICAL VALVE

CROSS-REFERENCE TO RELATED APPLICATION

This application is related to application Ser. No. 08/906, 358, assigned to the present assignee and filed concurrently herewith, the full disclosure of which is incorporated herein by reference.

BACKGROUND OF THE INVENTION

1. Field of the Invention

The present invention is generally related to surgical devices and methods, and in particular, provides a self-closing surgical valve capable of deforming to pass objects both proximally and distally, particularly for accessing an internal surgical site during laparoscopic and other minimally invasive surgical procedures.

Minimally invasive surgical procedures have gained wide acceptance in the areas of general and gynecological surgery. Minimally invasive techniques are now being developed for therapies of the heart, lung, kidney, and the like. Generally, these procedures make use of one or more small incisions (or other openings) to access internal tissues, often through a cannula, trocar, or other access device. Gas insufflation or fluid distension may be used to enhance the available space within the internal surgical site, and the therapy is often directed with reference to an image provided by an endoscope, a microscope, or using a remote imaging modality such as fluoroscopy, ultrasound, or the like. Generally, minimally invasive surgical procedures minimize patient trauma and speed recovery over traditional open surgical procedures.

Unfortunately, many surgical techniques are difficult to accomplish through laparoscopic cannulas or other minimally invasive access devices. It is sometimes desirable to remove relatively large masses of tissue, for example, to remove a kidney, a partial lung resection, or the like. Removing such large tissue masses laparoscopically through a small access lumen is fairly difficult and time consuming.

Specialized devices have recently been proposed to sever large tissue masses into segments, which are more easily removed. These devices generally include a rotating tube having a sharpened distal end which extends through a fixed outer tube. This sharpened end is inserted into the patient through a cannula, or directly through an incision. The surgeon inserts a grasping device (such as endoscopic forceps or a laparoscopic grasper) through the rotating tube. Grasping the large mass of tissue to be removed, the surgeon pulls the tissue up into the tube, so that the rotating edge severs the grasped portion from the large mass. The size of the severed tissue is generally limited by the outline of the rotating edge, so that the surgeon can continue to pull the severed tissue out of the patient through the rotating tube. By repeating the grasping and severing procedure, surgeons can remove relatively large masses of tissue quite quickly. As the large tissue mass is removed in small, individually grasped morcels, these devices are often referred to as "morcellators".

Although rotating tube morcellators represent a significant advancement in minimally invasive surgical procedures for removing large tissue masses, these known devices still have several significant drawbacks. It is often desirable to maintain pneumo-peritoneum (abdominal distention using pressurized gas) during the resection procedure. Although duck-bill and other laparoscopic valves are available to prevent the insufflation gas from flowing through the morcellator lumen, removal of tissues through these known self-closing valves is generally somewhat problematic. Specifically, duck-bill valves usually deform to pass graspers and other surgical implements distally through the morcellator, but work in connection with the present invention as shown that these duck-bill structures tend to catch on the large severed tissue morsels as they are drawn proximally through the valve. This can lead to failure of the valve and loss of pneumo-peritoneum, resulting in a considerable delay while the failed valve is removed and replaced and the abdomen is once again distended with insufflation gas.

In light of the above, it would be desirable to provide improved valve structures and sealing methods, particularly for use in minimally invasive surgical procedures. It would be particularly desirable if these improved valve structures were better adapted for passing objects both distally and proximally. It would further be desirable if such improved valve structures provided the pressure enhanced sealing and self-closure of known duck-bill valve structures, so as to be easily adapted for sealing insufflation gas during laparoscopy, and for a wide variety of additional minimally invasive surgical uses.

2. Description of the Background Art

Sealing structures for cannulas, trocars, and other minimally invasive surgical devices are described in U.S. Pat. No. 5,401,248, No. 5,391,153, No. 4,909,798, No. 5,603, 702, No. 5,180,373, No. 5,141,498, No. 5,514,098, No. 5,496,280, No. 5,441,486, No. 5,429,609, No. 5,397,314, No. 5,389,080, No. 5,385,552, No. 5,380,288, No. 5,356, 394, No. 5,354,280, No. 5,330,437, No. 5,312,362, No. 5,300,033, No. 5,269,764, No. 5,263,944.

SUMMARY OF THE INVENTION

The present invention provides methods and structures for sealing trocars, cannulas, laparoscopic morcellators, and other surgical devices. The valves of the present invention generally include a novel elastomeric sealing member having a cross-section which necks down from the valve lumen to a sealing slit, and which gradually returns outwardly and distally from the slit to the surrounding valve lumen. This dual taper lumen, which may resemble an hourglass from one side, can easily deform adjacent the slit to pass surgically implements distally, or to pass large bodies (such as severed tissue morsels) proximally. These valves will generally be self-closing, and a passage can be provided from distally of the slit to the outer surface of the elastomeric body adjacent the slit so that high pressures distally of the elastomeric body will tend to hold the slit closed when no implement traverses the valve.

The present invention generally provides a surgical valve comprising a tubular valve body having a lumen and defining a distal orientation and a proximal orientation. An elastomeric sealing member is disposed within the lumen of the valve body. The sealing member includes a plurality of segments which extend distally and inwardly from the lumen of the valve body. The first segments are sealable against each other. The sealing member further includes a second plurality of segments which extend distally and outwardly from the first plurality of segments toward the lumen of the valve body.

BRIEF DESCRIPTION OF THE DRAWINGS

FIG. 7 is a perspective view of an alternative laparoscopic morcellator having many of the same structures of the laparoscopic morcellator of FIG. 1, and in which the inner tube can slide axially within the cutting member to prevent inadvertent contact between the cutting edge and tissues, laparoscopic instruments, and the like.

DETAILED DESCRIPTION OF THE SPECIFIC EMBODIMENTS

The structures and methods of the present invention will significantly enhance the sealing of minimally invasive surgical access devices when objects pass both proximally and distally through the access device. These valves are suitable for maintaining hemostasis or fluid distention pressures, and will generally deform to pass surgical implements and other objects. The valves can then seal automatically when the objects are clear of the sealing member. Hence, the valves of the present invention are particularly well-suited for maintaining pneumo-peritoneum and other gas insufflation pressures during laparoscopic and other procedures. While the novel elastomeric sealing members of the present invention may be used for sealing of trocars, cannulas, access valves, and a wide variety of additional surgical structures, they will find their most immediate application for sealing laparoscopic morcellators during removal of large tissue masses from internal surgical sites.

Figure 1:
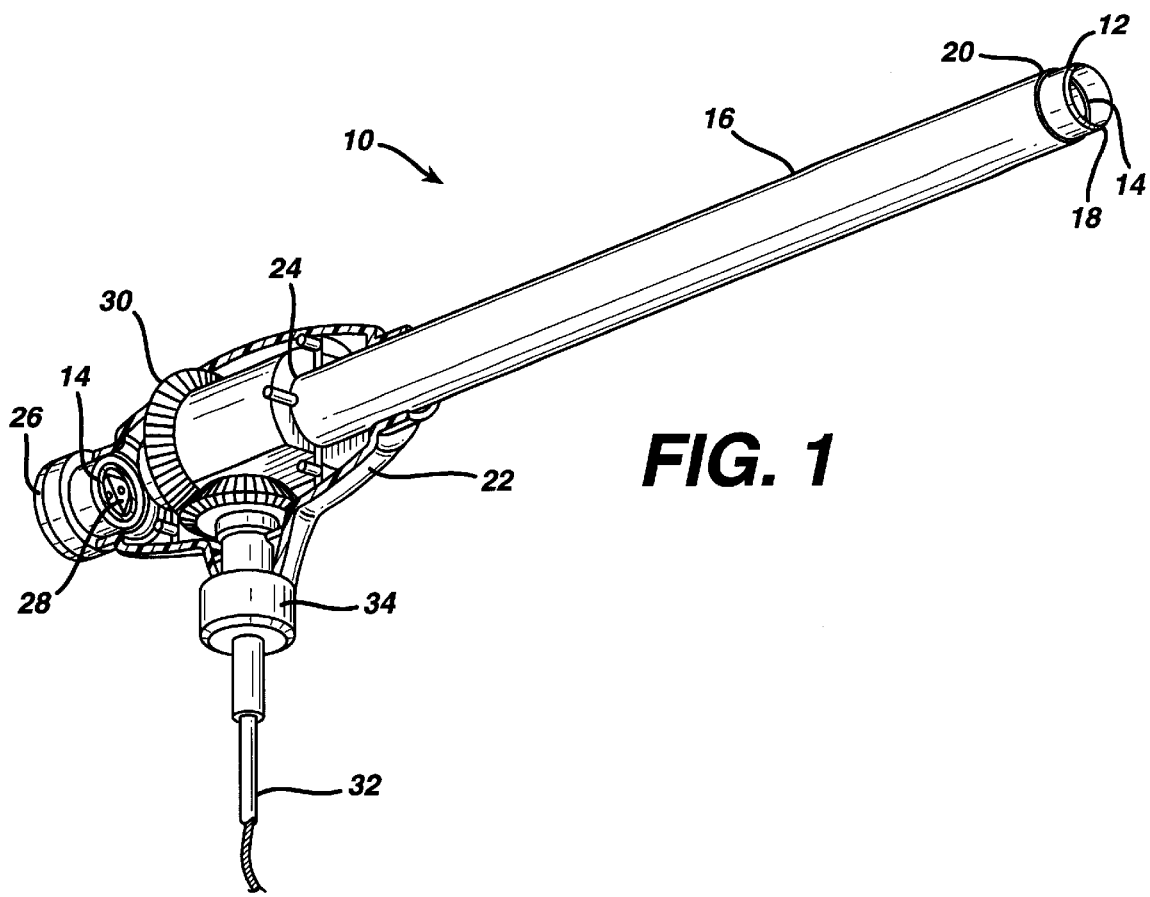
FIG. 1 is a perspective view of a laparoscopic morcellator according to the principles of the present invention, in which a portion of the housing is removed to show a mechanism for rotating a cutting tube between fixed inner and outer tubes, and in which a portion of the inner tube has been removed to show a valve within a lumen of the inner tube.

Referring now to FIG. 1, a disposable laparoscopic morcellator 10 includes a rotating tubular cutting member 12 disposed in the annular space between an inner tube 14 and an outer tube 16. A sharpened annular cutting edge 18 extends distally of a distal end 20 of the outer tube, while a proximal housing 22 is affixed to the proximal end 24 of the outer tube. The outer tube thereby prevents injury or twisting of morcellator 10 against the cannula surrounding the outer tube, against the skin, or against the tissue tract leading to the internal surgical site. Hence, the outer tube allows the physician to safely manipulate laparoscopic morcellator 10 when the tubular cutting member rotates.

Inner tube 14 is also affixed to housing 22. A proximal port 26 in the housing provides access to the lumen of the inner tube through a valve 28. Inner tube 14 is affixed to housing 22 proximally of a cutting tube drive mechanism 30, and extends distally into (and is supported by) the surrounding rotating cutting tube 12.

Drive mechanism 30 here comprises a pair of angled bevelled gears powered by a standard flex cable 32 through a flex cable coupler 34. The use of an external drive motor minimizes the weight and cost of morcellator 10, thereby making it feasible to provide a disposable morcellator structure. This avoids any need to use surgically sterilizable materials or a sharpenable cutting edge 18, and avoids long term wear between the tubes. Hence, the tubes may comprise inexpensive tube materials in simple sliding contact.

Inner tube 14, rotating cutting member 12, and outer tube 16 define a substantially rigid tubular structure in which the inner lumen of the inner tube is generally between about 0.25 and 0.9 inches in diameter, while the outer surface of outer tube 16 will preferably have a diameter of between about 0.3 and 1.0 inches. Rotating cutting member 12 will typically be formed of stainless steel, but may alternatively comprise other materials. Cutting edge 18 may be smooth or serrated. Inner tube 14 and outer tube 16 may comprise polymer or metallic structures, ideally being formed of fiber reinforced polymer. The tubes and cutting member will typically extend from housing 22 by a distance in the range between about 7.0 inches and 12.0 inches. Low friction coatings or lubrication may optionally be provided between the fixed tubes and cutting member 12, with friction ideally being limited by silicone lubricant.

Proximal housing 22 may comprise a metallic or polymeric structure, ideally being formed of polycarbonate. The beveled gears of drive mechanism 30 are supported by nylon bearings. The drive gear is coupled to flexible drive shaft 32 by coupler 34, while the driven gear is affixed to cutting member 12. Once again, the drive gears may comprise metallic or polymeric materials, ideally being formed of nylon. Such gears are commercially available from Winzeler of Chicago, Ill.

Figure 2:
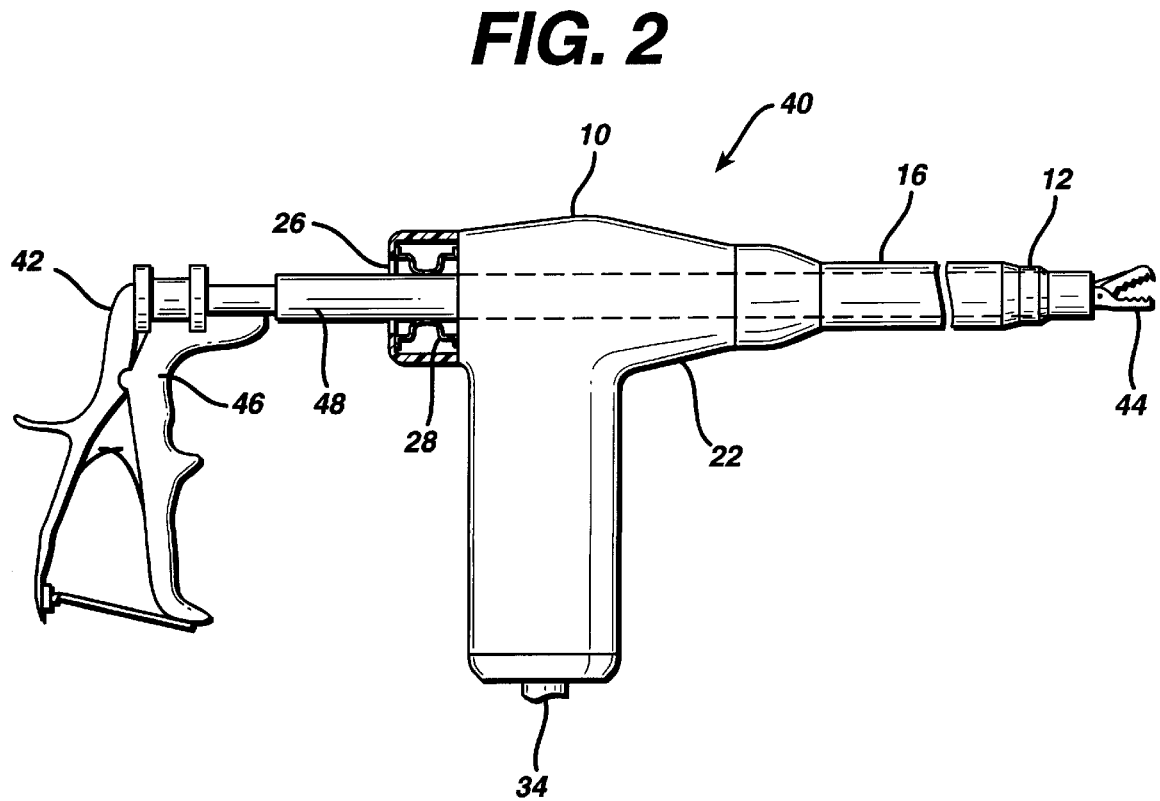
FIG. 2 is a side view of a laparoscopic tissue removal system, including the laparoscopic morcellator of FIG. 1 and an endoscopic grasper which has been inserted through the lumen of the inner tube.

Referring now to FIG. 2, a tissue removal system 40 generally includes morcellator 10 and a surgical instrument such as a laparoscopic grasper 42, laparoscopic forceps, or the like. Grasper 42 includes jaws 44 coupled to handle 46 by a shaft 48 so that actuation of the handle articulates the jaws for grasping tissue.

Jaws 44 are insertable through proximal port 26 and valve 28 into the lumen of the inner tube, and shaft 48 is generally longer than morcellator 10 so that the jaws can grasp tissues distally of cutting member 12. To minimize the loss of insufflation gas, the lumen of the inner tube may fittingly receive shaft 48. When grasper 42 is removed from morcellator 10, valve 28 substantially seals the lumen. Advantageously, the lumen of the inner tube does not rotate with the cutting member, so that contact between grasper 42 and the surrounding lumen will not twist handle 46 in the hands of the physician.

Figure 3:
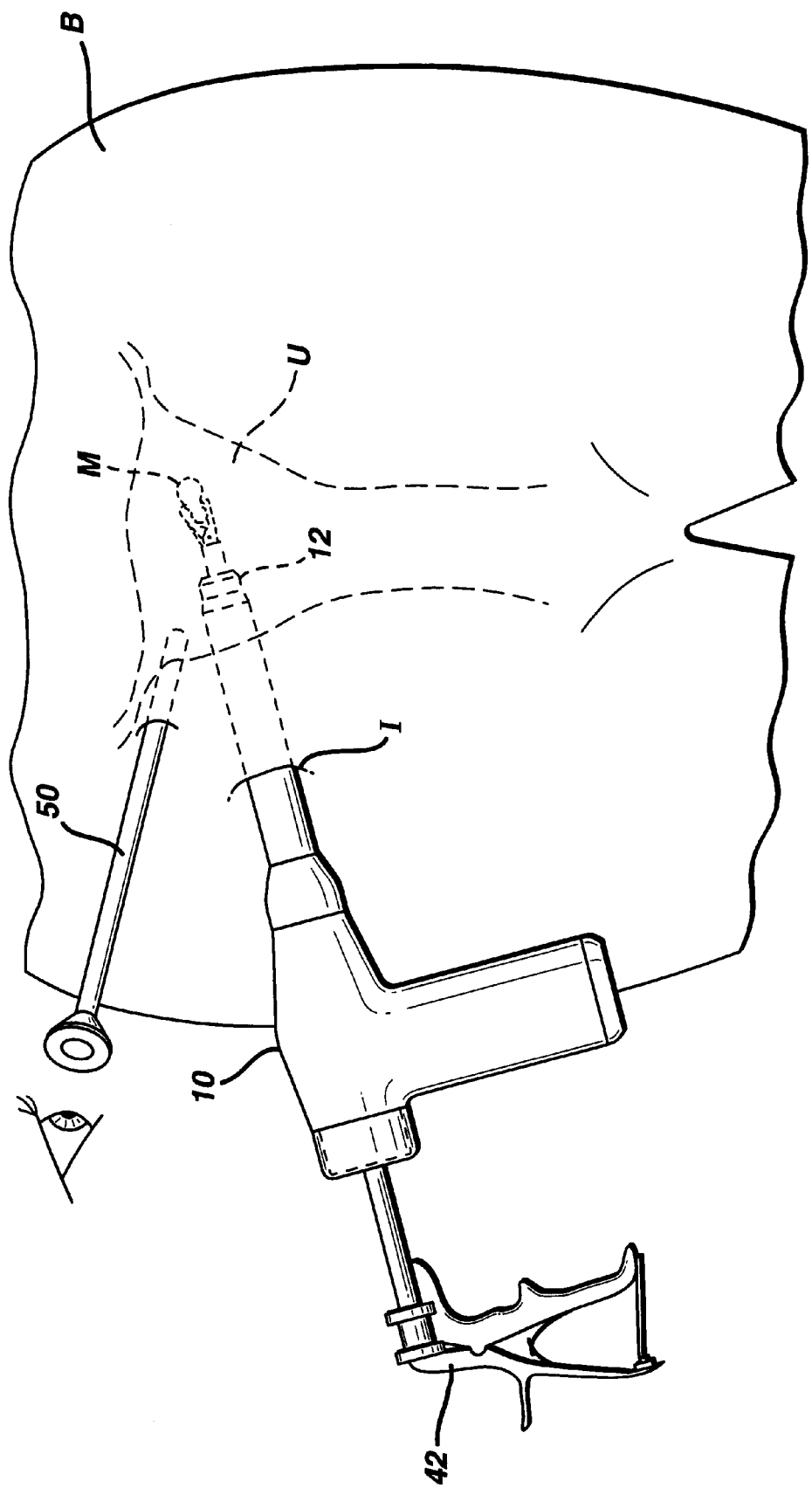
FIG. 3 illustrates the use of the laparoscopic morcellator of FIG. 1 for laparoscopic removal of a uterine myoma.
Figure 4A:
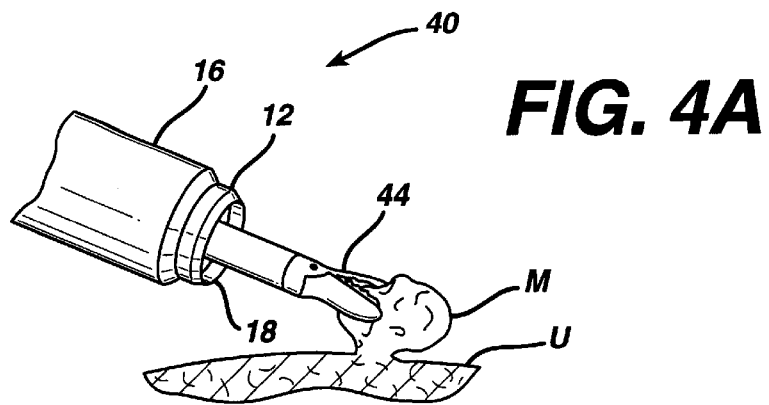
FIGS. 4A–C illustrate how the fixed internal tube of the laparoscopic morcellator of FIG. 1 prevents rotation or twisting of the grasped tissue morcel while the morcel is being withdrawn proximally through the rotating cutting tube.
Figure 4B:
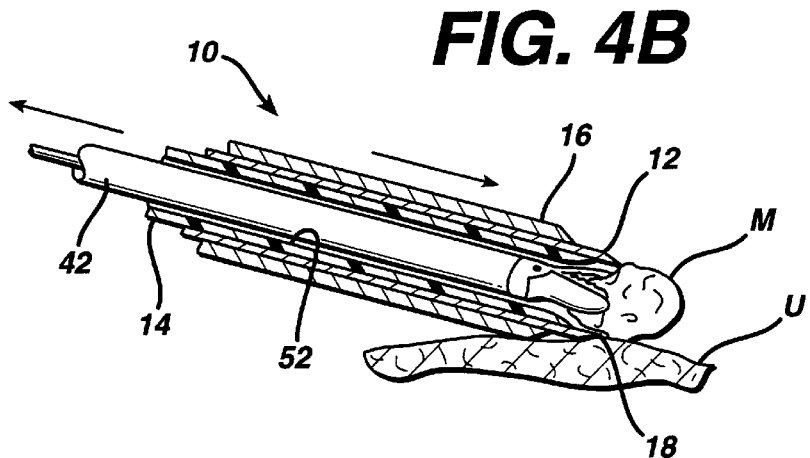
Figure 4C:
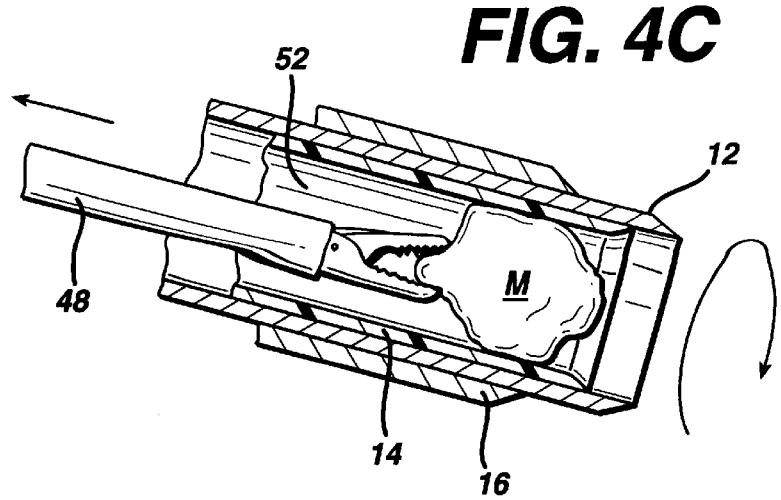

The use of tissue removal system 40 can be understood with reference to FIGS. 3–4C. As illustrated in FIG. 3, a uterus U of a patient body B is viewed using an endoscope 50, typically while the peritoneal cavity is distended under gas insufflation. Optical visualization may generally be provided using any of a variety of endoscopic structures, including telescopic and fiber optic laparoscopes, hysteroscopes, thoracoscopes, bronchioscopes, or the like, as appropriate for the particular tissue removal procedure. Alternatively, optical imaging capabilities may be incorporated into morcellator 10 or the associated surgical implement. Distension for some procedures may be provided using a clear liquid (such as sorbitol mannitol, saline, and the like), particularly for removal of intrauterine tissues. In some embodiments, the tissue removal procedure may be directed fluoroscopically, ultrasonically, under magnetic resonance imaging, or with some other remote imaging modality, so that no distension need be provided.

Morcellator 10 is inserted through an incision I to the internal surgical site. Cutting member 12 will typically not be rotating during insertion to minimize injury to tissues. An obturator may be inserted through the lumen of the inner tube and extend distally of morcellator 10 to help minimize trauma during insertion. Alternatively, the morcellator may be inserted through a cannula or other access device.

Grasper 42 is inserted into and through the lumen of morcellator 10, and is actuated by the physician to grasp myoma M targeted for removal. While myoma M is here shown as a relatively small protruding tissue structure, it should be understood that the method and system of the present invention are also well adapted for removing large masses of tissue by repeatedly grasping and severing target tissue portions.

As can be best understood with reference to FIGS. 4A–C, morcellator 10 is advanced distally and grasper 42 is withdrawn proximally so that myoma M is severed from uterus U by cutting edge 18 of rotating member 12. As myoma M is severed from the adjacent tissue, it is drawn into a lumen 52 of inner member 14, which does not rotate with rotating member 12. This avoids twisting of grasper 42 as the severed tissue is withdrawn proximally through the morcellator. Additionally, any contact between shaft 48 of grasper 42 and the surrounding lumen 52 will not deflect jaws 44 prior to severing of the tissue, thereby decreasing the potential for inadvertent injury to the adjacent tissue structures. Twisting of partially severed tissues is also minimized, so that cutting edge 18 can cleanly sever the grasped morcel from adjacent tissues with a minimum of trauma.

Figure 5:
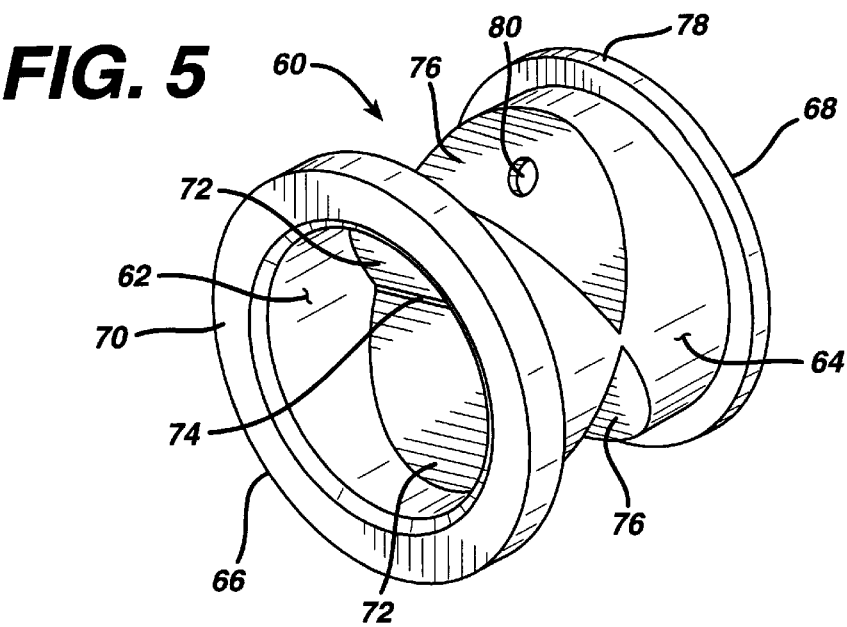
FIGS. 5–5C illustrate a valve for use in the laparoscopic morcellator of FIG. 1, in which a first pair of segments taper inwardly and distally to prevent leakage of insufflation gas when no instrument traverses the valve, and in which a second pair of segments taper outwardly and distally so that the valve easily passes tissue fragments drawn proximally through the morcellator.
Figure 5A:
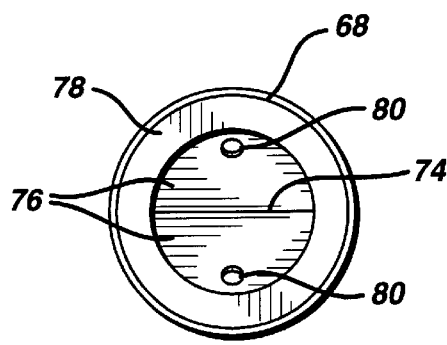
Figure 5B:
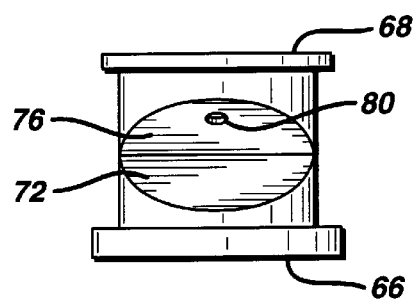
Figure 5C:
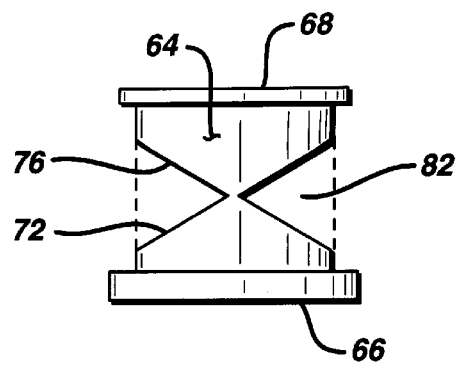

A particularly advantageous elastomeric sealing member 60 for valve 28 is illustrated in FIGS. 5–5C. Sealing member 60 generally comprises a tubular structure having an inner surface 62 and an outer surface 64. Sealing member 60 has a proximal end 66 and a distal end 68, and has an annulus 70 at the proximal end which sealingly engages the lumen of inner tube 14. It should be understood that this lumen may optionally be defined by housing 22 at the proximal end of morcellator 10 (see FIG. 1).

A first pair of segments 72 extend distally from annulus 70, and are angled inward, engaging each other along a slit 74. Taken alone, first segments 72 operate somewhat like a standard "duck-bill" valve, easily passing surgical instruments inserted distally through the valve. Slit 74 provides a gas tight seal when no instrument traverses the valve, and when a pressure on outer surface 64 of segments 72 is greater than a pressure on the inner surface 62 of these first segments.

Figure 6A:
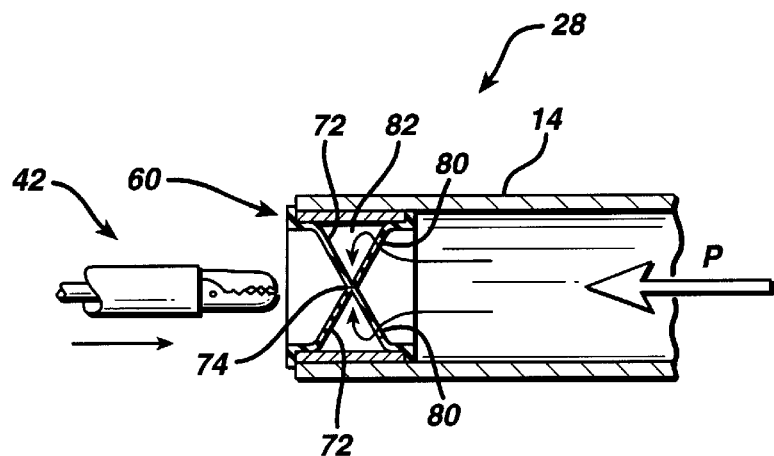
FIG. 6A illustrates how insufflation pressure is transmitted through openings in the distal segments of the valve of FIG. 5 to enhance sealing when no surgical instrument traverses the valve.
Figure 6B:
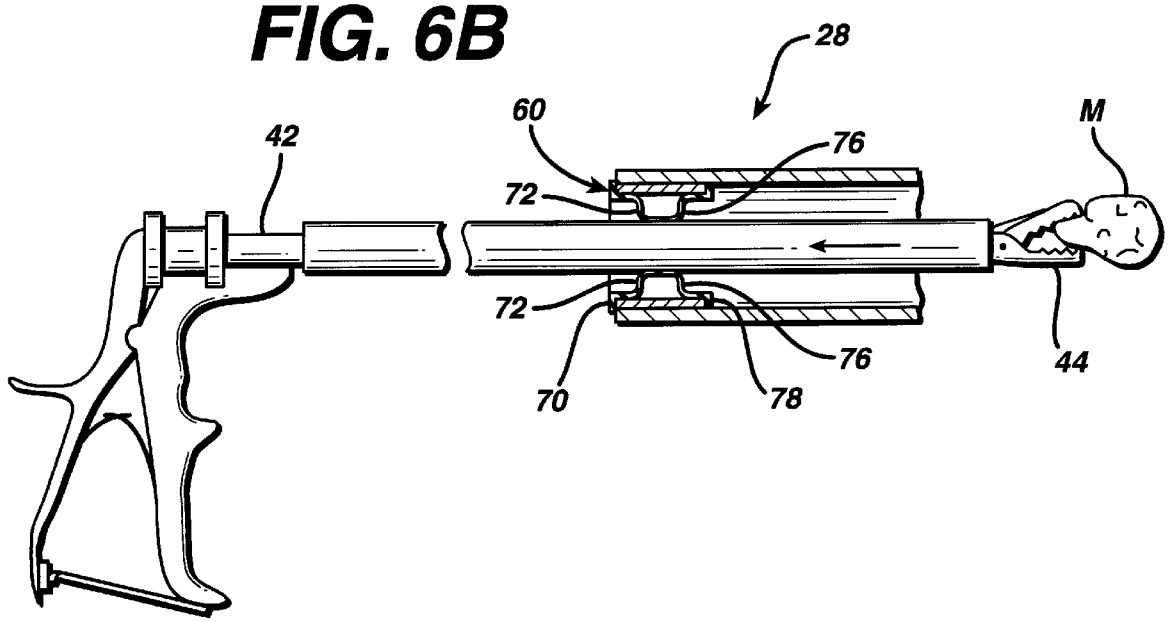
FIG. 6B illustrates how the distal segments of the valve of FIG. 5 facilitate proximal passage of a tissue morcel without everting the proximal valve segments.

Extending distally from first segment 72 are a pair of second segments 76. Second segments 76 angle distally and outwardly from slit 74 to a distal annulus 78. Each second segment has an opening 80 which allows gas pressure to pass through the second segments from distally of slit 74 to the outer surface 64 of first segment 72. In other words, an intermediate volume 82 (bordered by the adjacent first and second segments and by the surrounding lumen) is in fluid communication with the lumen of the valve distally of slit 74. Hence, when the pressure distally of the slit is higher than the proximal pressure, the first pair of segments will be pushed against each other by this pressure differential. This enhanced sealing is schematically illustrated in FIG. 6A, and is particularly advantageous for use with gas insufflation pressure P. Alternatively, elastomeric member 60 may find applications for maintaining a seal against pressurized liquid distension media, for maintaining hemostasis, and the like.

The ability of valve 28 having elastomeric member 60 to pass objects both proximally and distally can be understood with reference to FIGS. 6A and B. As with known duck-bill valves, segments 72 may be easily deformed to pass a surgical implement distally through slit 74. However, withdrawing a surgical instrument (such as grasper 42) proximally from known duck-bill valves often causes the valve to evert, so that at least a portion of the sealing segments are angled proximally rather than distally. Once the sealing segments of known duck-bill valves angle proximally, pressure P begins to push the slit open, rather than closed. Additionally, withdrawing enlarged structures (such as grasper 48 holding severed myoma M) proximally through known duck-bill valves can be difficult, as the angled valve segments tend to catch on any bulges. This is particularly problematic when withdrawing several individually severed tissue morcels, as the morcels (or portions thereof) may be pulled free from grasping jaws 44 to block the morcellator lumen.

Advantageously, second segments 76 of elastomeric body 60 provide a smooth transition between the distal lumen and slit 74. Second segments 76 also help support slit 74, preventing first segments 76 from everting as surgical implements and enlarged distal bodies are withdrawn proximally through the valve. In other words, the first and second segments provide a substantially contiguous lumen when elastomeric member 60 is deformed to open slit 74. This significantly improves the ability of the valve to seal after structures are withdrawn proximally, thereby enhancing the ability of the valve to maintain pneumo-peritoneum during a laparoscopic myomectomy.

Elastomeric member 60 may be formed of any suitable elastomeric material, such as rubber, latex, and the like, ideally comprising silicone. While first and second segments 72, 76 are here shown as substantially planar structures, they may alternatively be formed with some curvature. Similarly, while slit 74 here extends straight across the valve, it may alternatively be curved, Y-shaped, X-shaped, or the like, by changing the number and configuration of the first and second segments. The segments will generally be compliant enough to allow an instrument to pass through the valve, and sufficiently resilient to return to their original shape once the instrument is removed. The valve will generally be capable of passing any instrument having a size up to the inside diameter of the morcellator inner lumen. Typically, such instruments will have a size in the range from about 5.0 mm to about 10 mm in diameter.

Figure 7:
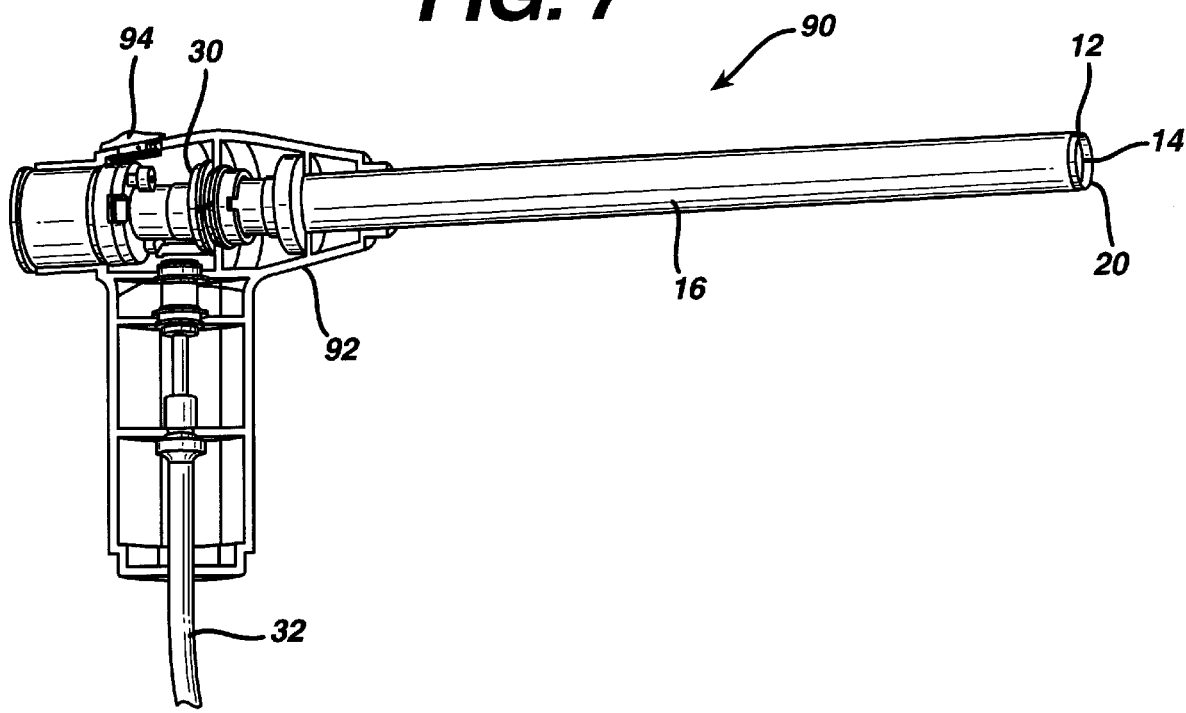
Figure 7A:
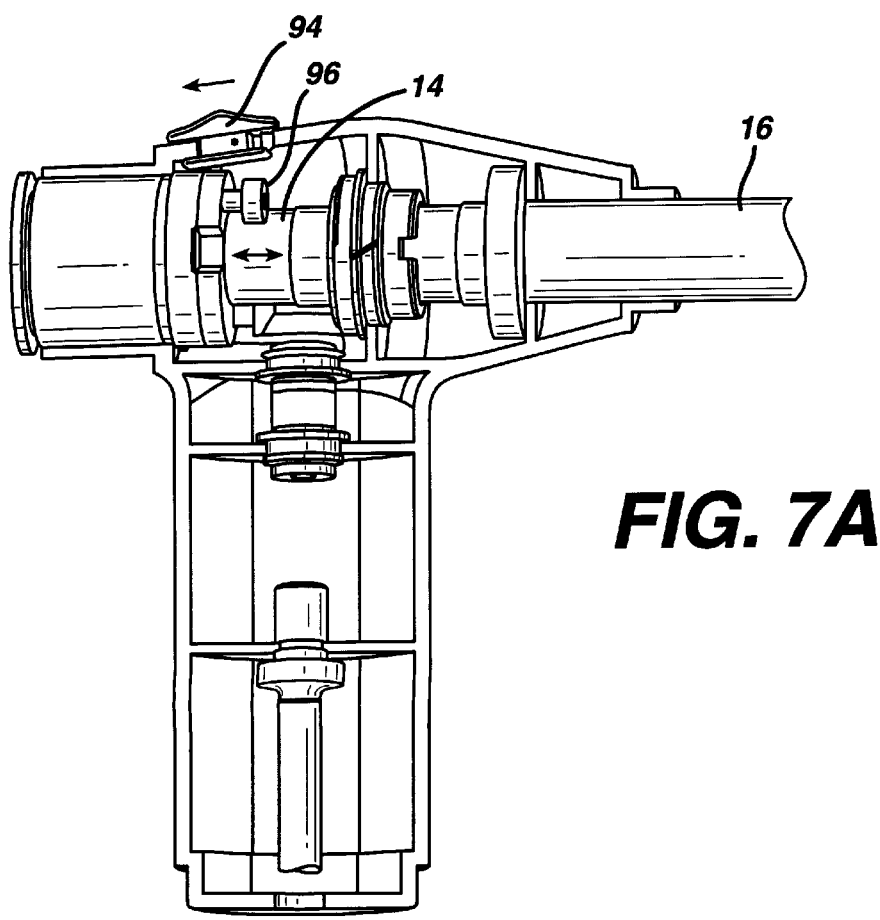
FIGS. 7A–7C illustrate an actuation mechanism and support structure for the axially sliding inner tube of FIG. 7, which allow the inner tube to act as a blade guard, according to the principles of the present invention.

Referring now to FIG. 7, an alternative laparoscopic morcellator 90 includes many of the same structural elements described above regarding laparoscopic morcellator 10 of FIG. 1. However, alternative morcellator 90 has a housing 92 which supports a guard actuator 94. As can be understood with reference to FIG. 7A, inner tube 14 is translatably supported by housing 92, so that sliding guard actuator 94 proximally retracts inner tube 14 relative to both outer tube 16 and rotating cutting tube 12. While inner tube 14 is in this proximal position, the distal end of the cutting tube extends distally beyond the inner and outer tubes 14, 16, as illustrated in FIG. 7, and as described above.

Figure 7B:
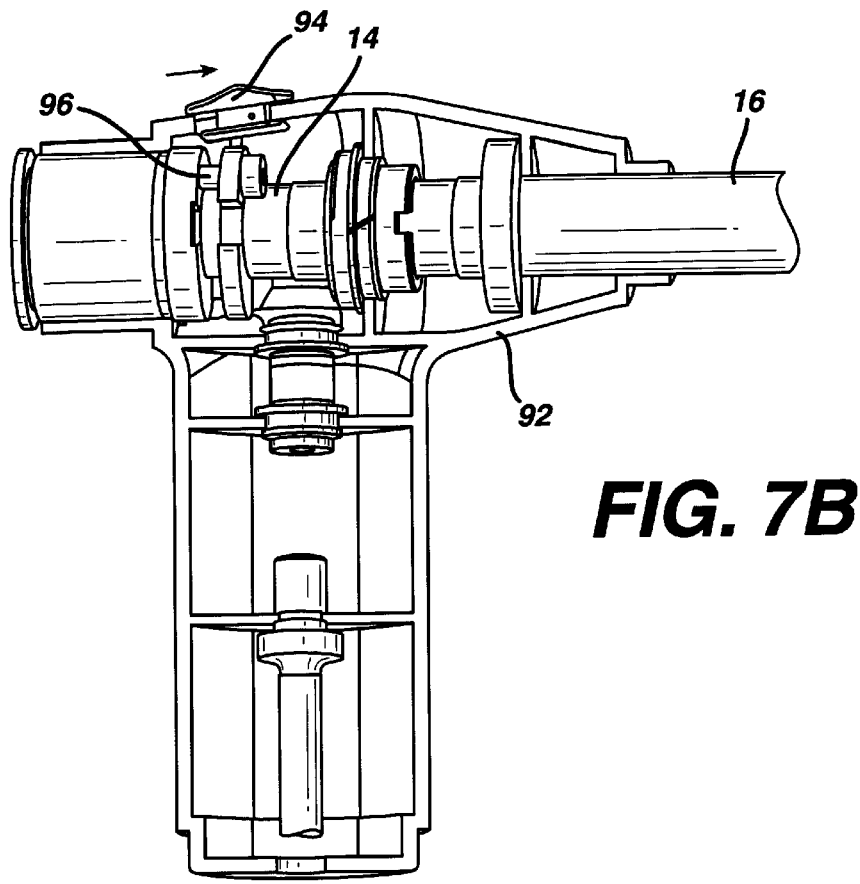
Figure 7C:
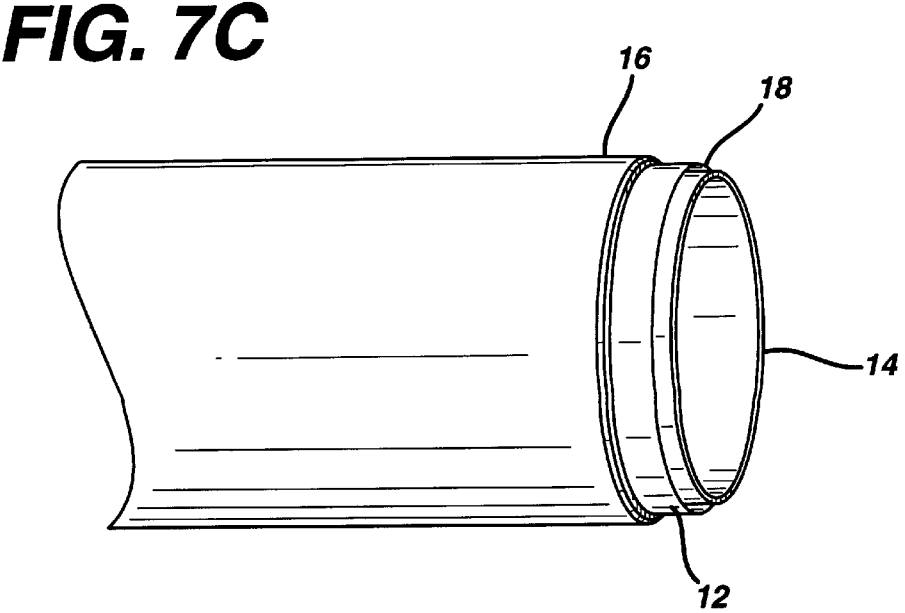

However, by sliding guard actuator 94 distally relative to housing 92, inner tube 14 is translated axially, as illustrated in FIG. 7B. With inner tube 14 in this distal position, the distal end of inner tube 14 extends distally of the sharpened cutting edge 18 of rotating member 12, as illustrated in FIG. 7C. Hence, inner tube 14 acts as a blade guard which protects the blade from inadvertent contact with other surgical instruments, and which also prevents inadvertent cutting of tissues during positioning and movement of the laparoscopic morcellator. As can be understood with reference to FIGS. 7A and 7B, inner tube 14 is rotationally fixed to housing 92 using pins 96. Advantageously, guard actuator 94 can be advanced distally to protect the cutting edge and surrounding tissues during insertion of the laparoscopic morcellator, during removal of the system after the laparoscopic procedure is finished, and intermittently between insertion and removal of the morcellator as desired by the surgeon.

While the exemplary embodiments of the present invention have been described in considerable detail, by way of illustration and for clarity of understanding, a number of modifications, adaptations, and changes will be obvious to those of skill in the art. Therefore, the scope of the present invention is limited solely by the appended claims.

What is claimed is:

1. A surgical valve comprising:
    a tubular valve body having a lumen and defining a distal orientation and a proximal orientation; and
    an elastomeric sealing member disposed within the lumen of the valve body, the sealing member including:
        a first plurality of segments extending distally and inwardly from the lumen of the valve body, the first segments sealable against each other, the first segments having distally oriented surfaces and proximally oriented surfaces, the distal surfaces angled so that a greater pressure along the distal surfaces than the proximal surfaces pushes the first segments together to enhance sealing; and
        a second plurality of segments extending distally and outwardly from the first plurality of segments toward the surrounding lumen of the valve body, the second plurality of segments having at least one opening therethrough from a distally oriented surface to a proximally oriented surface, the at least one opening transmitting the pressure from within the lumen of the valve body proximally through the second segments and against the distal surfaces of the first segments.

2. A surgical valve as claimed in claim 1, wherein the greater pressure along the distal surfaces than the proximal surfaces pushes the first segments together along a slit.

3. A surgical valve as claimed in claim 2, wherein the sealing member sealingly engages the lumen of the valve body proximally of the first segments.

4. A surgical valve as claimed in claim 1, wherein the sealing member further comprising a first annulus proximal of the first segments and a second annulus distal of the second segments to affix and seal the sealing member along the lumen of the valve body proximally and distally of the segments.

5. A surgical valve as claimed in claim 4, wherein inner surfaces of the second segments extend distally from inner surfaces of the first segments so that objects passing proximally and distally through the valve deform the sealing member along a substantially contiguous sealing member lumen.

6. A surgical valve comprising:
    a tubular valve body having a lumen and defining a distal orientation and a proximal orientation;
    a sealing member disposed within the lumen of the valve body, the sealing member including an elastomeric tubular body having:
        a proximal portion which sealingly engages the surrounding valve body lumen;
        a first pair of segments angled inwardly and distally from the proximal portion and sealingly engaging each other along a slit;
        a second pair of segments angled outwardly and distally from the first segments adjacent the slit, each of the segments having an opening therethrough; and
        a distal portion attached to the valve body lumen;
    the valve body and the segments of the sealing member defining two intermediate volumes therebetween, each intermediate volume being in fluid communication with the lumen of the valve body distally of the slit through the opening of an adjacent second segment so that a greater pressure distally of the slit than proximally of the slit enhances sealing of the slit.

7. A surgical valve as claimed in claim 6, wherein inner surfaces of the second segments extend distally from inner surfaces of the first segments so that objects passing proximally and distally through the valve deform the sealing member along a substantially contiguous sealing member lumen.

* * * * *